United States Patent [19]

Chen

[11] Patent Number: 5,221,622

[45] Date of Patent: Jun. 22, 1993

[54] 170KD MEMBRANE-BOUND PROTEASE USEFUL IN DIAGNOSIS OF MALIGNANT CELLULAR TRANSFORMATION

[75] Inventor: Wen-Tien Chen, Washington, D.C.

[73] Assignee: The Board of Regents of Georgetown University, Washington, D.C.

[21] Appl. No.: 596,049

[22] Filed: Oct. 11, 1990

[51] Int. Cl.$^5$ ............................ C12N 9/64; C12N 9/50
[52] U.S. Cl. .................................... 435/226; 435/219; 530/828
[58] Field of Search ................. 435/219, 226; 530/828

[56] References Cited

U.S. PATENT DOCUMENTS 4,816,400  3/1989  Tryggvason et al. .............. 435/219

OTHER PUBLICATIONS

Chen et al, J. of Cell Biology, vol. 98, Apr. 1984, pp. 1546–1555.
Baici et al, Invasion Metastasis, 4:13–27 (1984).
Chen et al, Proc. Natl Acad. Sci, Nov. 1990, 87(21) pp. 8296–8300.

Primary Examiner—David M. Naff
Assistant Examiner—Susan M. Weber
Attorney, Agent, or Firm—Oblon, Spivak, McClelland, Maier & Neustadt

[57] ABSTRACT

A novel 170 kD membrane protease is isolated from malignant human melanoma cell line LOX and RPMI7951. The protease is useful in a method of diagnosing cellular transformation.

4 Claims, 15 Drawing Sheets

LOX 1d

RPMI7951 1d

SKMEL28 1d

FIG. 7

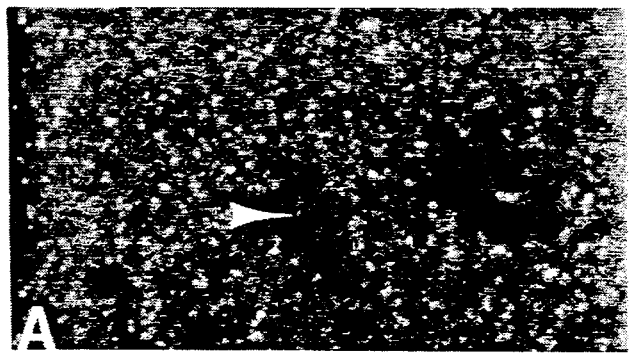
FIG. 8A
LOX
FIG. 8B
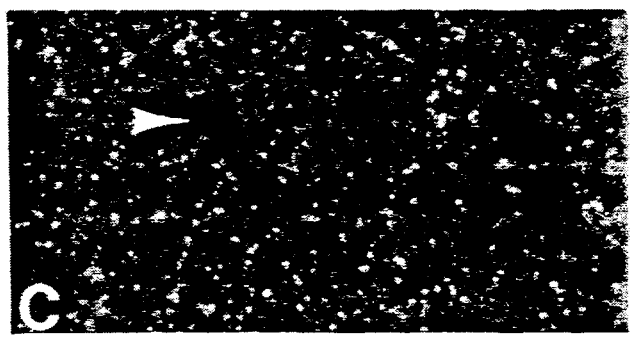
FIG. 8C

RPMI7951

D

SKMEL28

F

170KD MEMBRANE-BOUND PROTEASE USEFUL IN DIAGNOSIS OF MALIGNANT CELLULAR TRANSFORMATION

BACKGROUND OF THE INVENTION

1. Field of the Invention

The present invention is directed to a novel membrane protease isolated from malignant human melanoma cells such as the LOX line and RPMI7951 line. The invention is further directed to diagnosis of cellular transformation involving the use of this protease.

2. Background of the Invention

The invasion of tumor cells through surrounding connective tissue is an important stage of metastasis requiring cell surface protease activity (Jones, P. A., and DeClerck, Y. A. (1980), Cancer Res. 40, 3222-3227; Chen, W.-T., Olden, K., Bernard, B. A. and Chu, F.-F. (1984), J. Cell Biol. 98, 1546-1555). Tumor cell invasiveness has been linked with an increased production of extracellular matrix (ECM)-degrading enzymes, including plasminogen activators (for a review see Dano, K., Behrendt, N., Lund, L. R., Ronne, E., Pollanen, J., Salonen, E. M., Stephens, R. W., Tapiovaara, H., and Vaheri, A. (1989), Cancer Metastasis V. Schirrmacher R. Schwartz-Albiez (Ed.s) Springer Verlag Berlin, pp. 98-107), lysosomal cysteine proteases (Poole, A. R., Tiltman, K. J., Recklies, A. D., and Stoker, T. A. (1980), Nature 273, 545-547; Sloane, B. F., Rozhin, J., Johnson, K., Taylor, H., Crissman, J. D., and Honn, K. V. (1986), Proc. Natl. Acad. Sci. U.S.A., 83, 2483-2487), collagenases (Liotta, L. A., Abe, S., Robey, P. G., and Martin, G. R. (1979), Proc. Natl. Acad. Sci., U.S.A., 76, 2268-2272), and glycosidases (Nakajima, M., Irimura, T., DiFerrante, N., and Nicolson, G. L. (1984), J. Biol. Chem. 259, 2283-2290). Very little attention, however, has been paid to membrane proteases.

Plasma membrane-associated proteases have been identified from biochemically defined "membrane" fractions, which were derived from mixed cell types in tissues (Almenoff, J., and Orlowski, M. (1983), Biochemistry 22, 590-599; Malfroy, B., Schofield, P., Kuang, W. J., Seeburg, P. H., Mason, A. J., and Henzel, W. J. (1987), Biochem. Biophys. Res. Commun. 144, 59-66; Tanaka, K., Nakamura, T., and Ichihara, A. (1986), J. Biol. Chem. 261, 2610-2615). Studies from some tumors have shown that solid tumors contain heterogeneous cell types, and invading tumor cells represent less than 1/10,000 of the population (Poste, G., Doll, J., Hart, H., and Fidler, I. J. (1980), Cancer Res. 40, 1636-1644). Thus, attempts to identify these proteases from in situ solid tumors have not been successful.

Isolation of membrane proteases from tumor cells in culture that contain a homogeneous population, has shown some important results. Cell fractionation has localized cathepsin B-like activity to the plasma membrane of tumor cells (Sloane, B. F., Rozhin, J., Johnson, K., Taylor, H., Crissman, J. D., and Honn, K. V. (1986), Proc. Natl. Acad. Sci. U.S.A., 83, 2483-2487). A chymotrypsin-like protease activity was also identified from tumor cell membranes (Yavelow, J., Caggana, M., and Beck, K. A. (1987), Cancer Res. 47, 1598-1601; Zucker, S., Wieman, J. M., Lysik, R. M., Wilkie, D., Ramamurthy, N. S., Golub, L. M. and Lane, B. (1987), Cancer Res. 47, 1608-1614). In addition, the 100 kD common acute lymphoblastic leukemia antigen (CALLA) has been identified as neutral endopeptidase 24.11, an integral, zinc metalloendoproteinase (Shipp, M. A., Vijayaraghavan, J., Schmidt, E. V., Masteller, E. L., D'Adamio, L., Hersh, L. B., and Reinherz, E. L. (1989), Proc. Natl. Acad. Sci. U.S.A., 86, 297-301), which may be identical to the neutral metalloendoprotease purified from the detergent-extracted membrane fraction of rabbit kidney tissue (Almenoff, J., and Orlowski, M. (1983), Biochemistry 22, 590-599).

Previously, plasminogen activator was localized on the cell surface of Rous sarcoma virus (RSV)-transformed cells (Quigley, J. P. (1976), J. Cell Biol. 71, 472-486) and was shown to be involved in tumor metastasis (Ossowski, L., and Reich, E. (1983), Cell 35, 611-619). L. B. Chen and Buchanan (Chen, L. B., and Buchanan, J. M. (1975), Proc. Nat. Acad. Sci. U.S.A., 72, 1132-1136), however, showed that plasminogen-independent fibrinolysis of cell surface proteins involved unidentified proteases produced by transformed cells. It has also been shown that RSV-transformed cells express invasiveness by locally degrading fibronectin crosslinked gelatin films at rosette contact sites or invadopodia (Chen, W.-T., Olden K. Bernard, B. A. and Chu, F.-F. (1984), J. Cell Biol. 98, 1546-1555; Chen, W.-T., Chen, J. M., Parsons, S. J., and Parsons, J. T. (1985), Nature (Lond.) 316, 156-158; Chen, W.-T. (1989), J. Exptl. Zool. 251, 167-185). The transformed cells express 120 kD and 150 kD proteases in association with the membrane, which degrade fibronectin (Chen, J.-M. and Chen, W.-T. (1987), Cell 48, 193-203). These proteases are present in extremely low quantity and the possibility that these proteases are associated with viruses in the RSV transformation model is difficult to rule out.

Crosslinked gelatin films comprising fluorescent and radiolabeled proteins covalently coupled to the surface of the substratum have been developed (Chen, W.-T., Olden, K., Bernard, B. A. and Chu, F.-F. (1984), J. Cell Biol. 98, 1546-1555). This technique allows identification of tissue culture cells which express activated ECM-degrading proteases at sites of contact between cells and their substrata.

SUMMARY OF THE INVENTION

The present invention is directed to a 170 kD protease which is isolated from the human amelanotic melanoma cell line LOX which is known and available to the public (Fodstad, O., Aamdal, S., Mcmenamin, M., Nesland, J. M., and Pihl, A. (1988), Int. J. Cancer 41, 442-449), and from the human malignant melanoma cell line RPMI7951 which is deposited in the American Type Culture Collection (deposit number ATCC HTB66, by Moore, G. (1977), J Nat. Cancer Inst. 59, 301-307). This protease is implicated in the local degradation of fibronectin and collagen substrates in vitro. The protease is expressed by malignant transformed, extracellular matrix invasive cells, but not corresponding normal cells or other malignant cells. SK-MEL28, a cell line originating from human melanotic melanoma, was used as the control for cell invasiveness because it has a more differentiated phenotype (Carey, T. E., Takahashi, T., Resnick, L. A., Oettgen, H. F. and Old, L. J. (1976), Proc. Natl. Acad. Sci. U.S.A., 73, 3278-3282).

The present invention is directed to a method of identifying the 170 kD protease from the tumor and the plasma of LOX tumor-bearing athymic nude mice. This protease is related to tumor progression in nude mice.

The invention is also directed to a method for the early detection of human cancers using the procedures described below which specifically identify the 170 kD protease present in the plasma of cancer patients for detecting early cancer formation and for its temporal association with tumor depression, as well as its expression in tumor biopsies upon malignant effusion.

These and other objects of the present invention which will readily become apparent from the following specification have been accomplished by discovering and purifying a membrane-associated protease from human melanoma cell line LOX.

DESCRIPTION OF THE DRAWINGS

A more complete appreciation of the invention and many of the attendant advantages thereof will be readily obtained as the same becomes better understood by reference to the following detailed description when considered in connection with the accompanying drawings.

DIC images of cell cultures show surface indentations on the film formed under LOX cells but not SK-MEL28 cells. Bar, 50 μm.

Figure 2B:
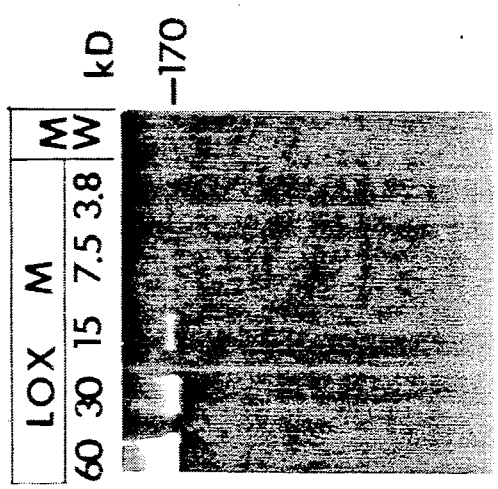
Figure 2A:
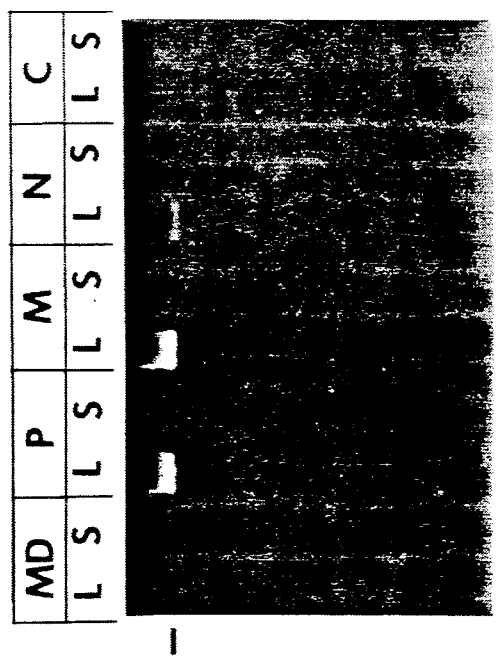

FIG. 2A and FIG. 2B show the identification of a 170 kD protease in subcellular fractions of LOX (L) and SK-MEL-28 (S) cells.

FIG. 2A shows a gelatin zymogram of various subcellular fractions from LOX (L) and SK-MEL28 (S).

These fractions include concentrated serum-free conditioned media (MD), octylglucoside detergent extract of the 100,000 xg pellet from conditioned media (P), detergent-soluble membrane fraction (M), detergent-soluble nuclear fraction (N), and cytosol fraction (C), which were prepared in solutions containing 5 mM EDTA. Approximately 30 μg of total proteins were applied to each lane and subjected to gelatin zymography. Only the membrane derived from conditioned media (P) and membrane fraction (M) of LOX cells show a major negatively-stained band with apparent Mr of 170 kD that represents complete digestion of immobilized gelatin by the protease. The 170 kD protease is also present in a small amount in the membranes from cellular fragments in nuclear fraction (N), but not in the media (MD) and the cytosol (C).

FIG. 2B shows enzymatic activities of the membrane from LOX cells.

The detergent-soluble membrane fraction of LOX cells (M) was serially diluted and analyzed on a gelatin zymogram. Each lane contains the amount of total proteins as indicated. The gelatin zymogram shows that in the lane containing 30 μg of total proteins a prominent band at 170 kD is apparent. MW indicates the lane containing molecular weight standards.

Figure 3:
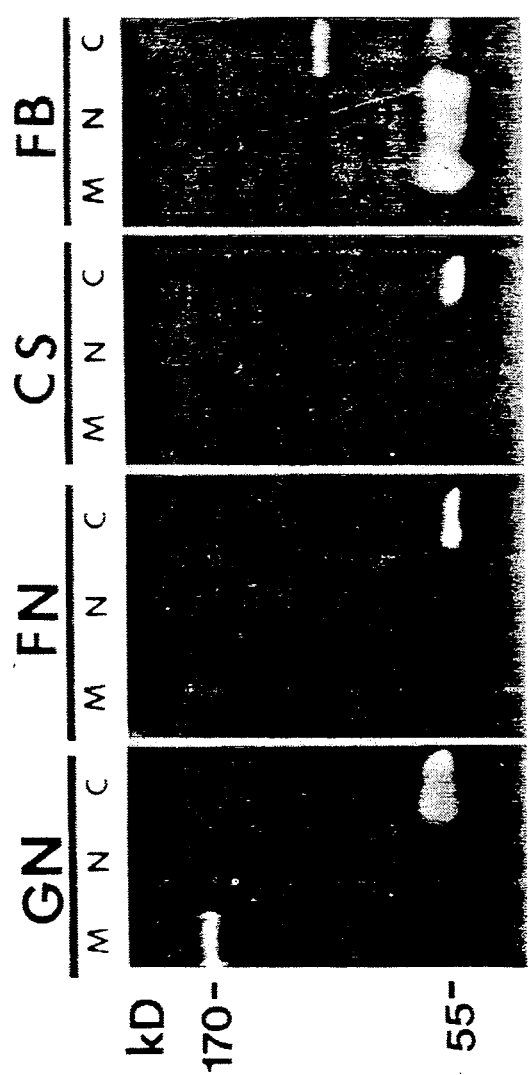

FIG. 3 shows the association of a 170 kD gelatinase and a 55 kD plasminogen activator with LOX membranes.

The detergent-soluble membrane fraction (M), detergent-soluble nuclear fraction (N), and cytosol fraction (C) were used to produce zymograms on gelatin (GN), human plasma fibronectin (FN), and casein (CS) substrate. In addition, these cellular extracts were also analyzed for plasminogen-dependent proteolysis using fibrin (FN) gel overlay in the presence of plasminogen (indicated as FB at the right panel) and the absence of plasminogen. Approximately 30 μg of total proteins were loaded on each lane. Only the membrane fraction (M) showed the 170 kD protease on the gelatin (GN) gel. However, the 170 kD band was not found in other fractions on the gelatin (GN) gel, nor in any of the fractions on fibronectin (FN), casein (CS) and fibrin (FB) gels. In this experiment a 55 kD metalloprotease (sensitive to EDTA) was found in the cytosol fraction (C) which can degrade gelatin, fibronectin, and casein. In the fibrin (FB) overlay gel, a 55 kD plasminogen activator was identified in association with the membrane of detergent-soluble membrane fraction (M) and detergent-soluble nuclear fraction (N). The 55 kD plasminogen activator, however, was not active in the fibrin gel lacking plasminogen. In addition, a 110 kD fibrin-degrading protease was identified in the cytosol fraction (C).

Figure 4A:
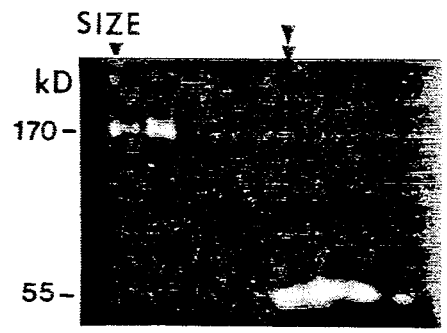
Figure 4B:
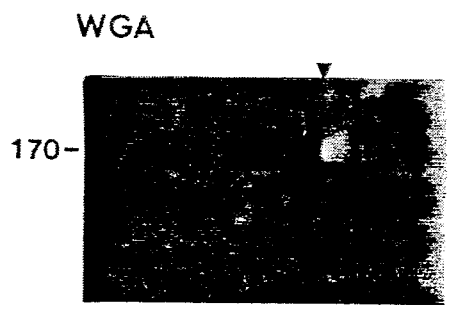
Figure 4C:
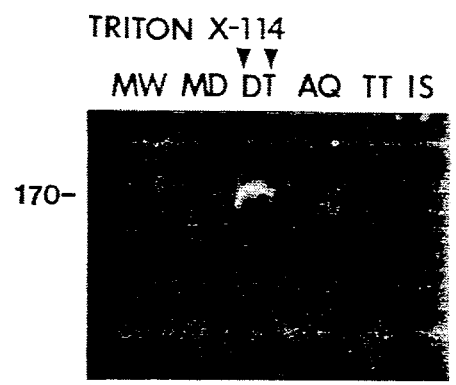

FIGS. 4A, 4B and 4C show the partial purification of a 170 kD protease as assayed on gelatin zymograms.

FIG. 4A shows the results of a Sephacryl S-200 gel filtration of the detergent-soluble membrane fraction from LOX cells.

Each fraction volume was 2.4 ml and fraction 12 was the onset of the void volume (single arrowhead). Approximately 10 μg of total proteins from each fraction were loaded in each lane of the gelatin zymogram, and the 170 kD protease was detected from fractions 12 (single arrowhead) to 14 in an approximate 3-fold increase in specific activity over the starting extract. This procedure separates the 170 kD protease from the 55 kD metalloprotease (right double arrowheads). The 55 kD band was not observed in preparations with $NaN_3$ and EDTA.

FIG. 4B shows the results of wheat germ aglatinin (WGA)-agarose affinity chromatography of the 170 kD protease.

Fractions 12 to 14 from the Sephacryl S-200 gel filtration were pooled and analyzed by WGA-agarose affinity chromatography. The WGA-binding proteins were eluted with 0.5 M N-acetyl-D-glucosamine. Approximate 1 μg of total protein from each fraction were loaded in each lane of the gelatin zymogram, and the 170 kD protease was detected from fractions 13 (arrowhead) to 15. The 170 kD was enriched 10-fold in specific activity over that of the material loaded onto the column.

FIG. 4C shows Triton X-114 phase partitioning of the detergent-soluble material recovered from LOX cells.

Molecular weight markers were loaded in the first lane (MW). Subsequent lanes contained concentrated serum-free conditioned media (MD), the detergent phase (DT) and aqueous phase (AQ) of the Triton X-114 detergent extract of the LOX cell layer, Triton X-114 detergent extract of the LOX cell layer (TT), and the insoluble material from the Triton X-114 detergent extract of the LOX cell layer (IS). Approximately 30 μg of total proteins were applied to each lane and subjected to gelatin zymography. The 170 kD protease was partitioned into the detergent phase of the Triton X-114 extracts (DT, double arrowheads), concentrating the 170 kD activity 10-fold over that of the total Triton X-114 detergent extract of the LOX cell layer (TT).

Figure 5A:
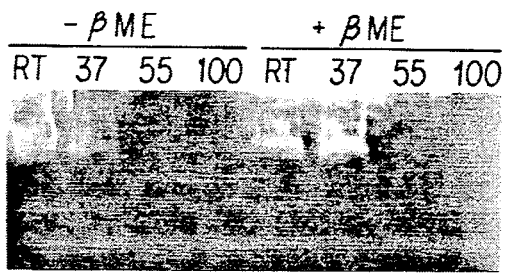
Figure 5B:
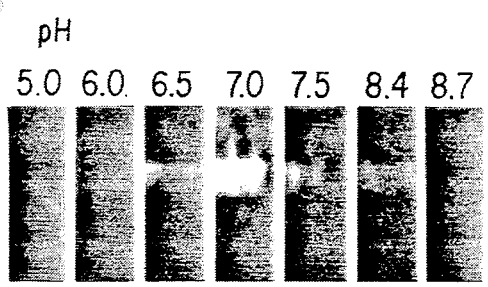
Figure 5C:
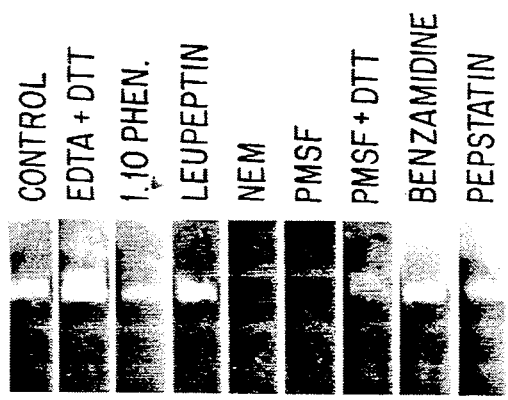

FIGS. 5A, 5B and 5C show the characterization of the 170 kD protease on gelatin zymograms.

FIG. 5A shows the effects of heating and the reducing agent β-mercaptoethanol on the activity of 170 kD protein.

Approximate 60 μg of total proteins were mixed with Laemmli's sample buffer with or without 2.5% β-mercaptoethanol (βME), and incubated at various temperatures as indicated before being subjected to gelatin zymography. Treatment of samples are indicated as: +βME, samples in the buffer containing 2.5% β-mercaptoethanol; −βME, samples in the buffer without β-mercaptoethanol; RT, room temperature (22° C.) for 1 h; 37: 37° C. for 1 h; 55: 55° C. for 10 min; 100: boiling for 2 min. The 170 kD gelatinase was active in the samples incubated at room temperature and at 37° C., whereas it was inactivated after incubation at 55° C. for 10 min or boiling for 2 min. The 170 kD activity was slightly enhanced by βmercaptoethanol, but without significant change in the electrophoretic mobility.

FIG. 5B shows the optional pH range of the 170 kD gelatinase.

Slices of gelatin gels containing the 170kD protease were prepared and incubated in Hanks' balanced salt solution (HBSS; 0.4 mM $Na_2HPO_4$, pH 7.5/0.5 mM $KH_2PO_4$/5.25 mM KCl/1.25 mM $CaCl_2$/0.8 mM $MgSO_4$/136 mM NaCl) buffered at the indicated pH. The 170 kD gelatinase was active in the range from pH 6 to pH 8.4, with its optimal pH at pH 7.

FIG. 5C shows inhibitor specificities of the 170 kD protease.

Prior to electrophoresis, the detergent soluble membrane fractions from LOX cells were treated with various protease inhibitors as described below. Concentrations of inhibitors were as follows: EDTA 2 mM, DTT 2 mM, 1,10 phenanthroline 2 mM, leupeptin 0.1 mM, NEM 1 mM, PMSF 1 mM, benzamidine 10 mM, pepstatin 0.03 mM. In the lane marked PMSF+DTT, the sample was preincubated with 1 mM PMSF, and after electrophoresis the gel slice was incubated in HBSS containing 10 mM DTT. The 170 kD activity was enhanced by incubating with a mixture of 2 mM EDTA and 2 mM DTT. The 170 kD protease was inhibited by NEM or PMSF, but PMSF inhibition could be partially recovered by incubating with DTT. The 170 kD protease was not inhibited by 2 mM 1,10 phenanthroline, 0.1 mM leupeptin, 10 mM benzamidine, or 0.03 mM pepstatin.

Figure 6:
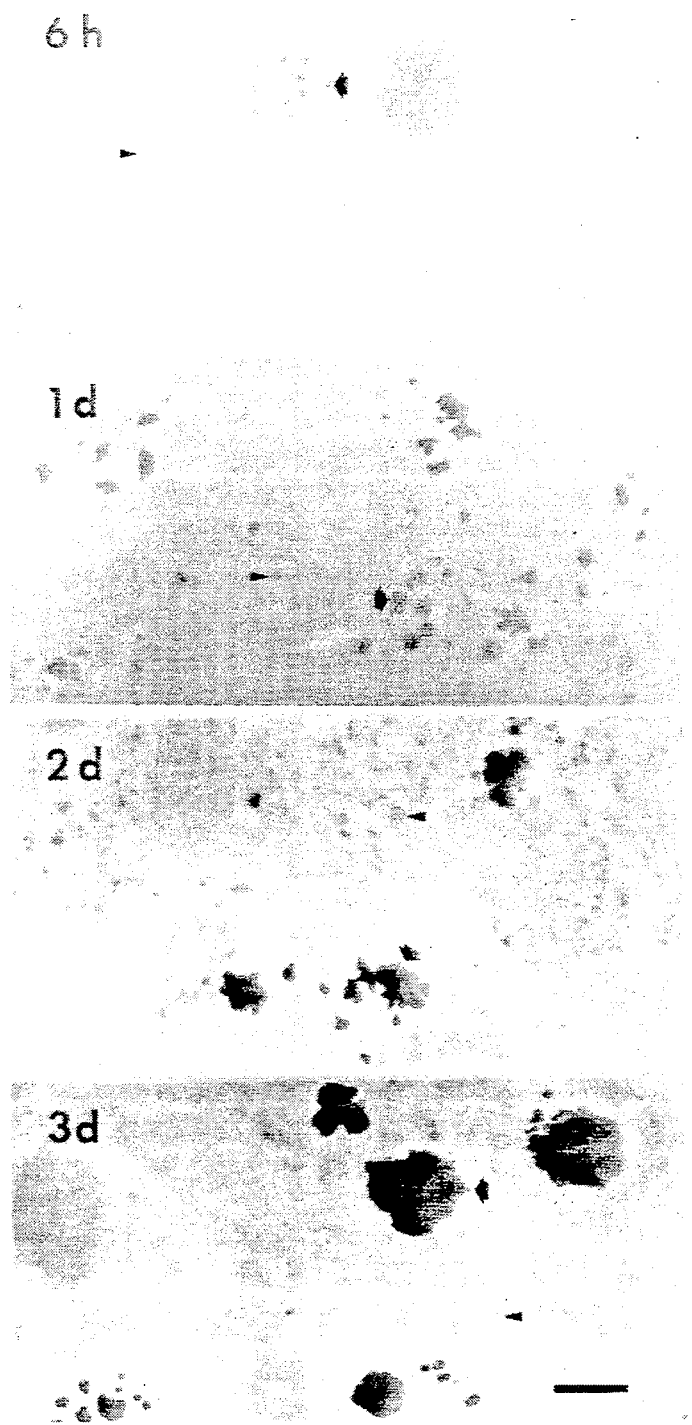

FIG. 6 shows an immunofluorescent visualization of the local degradation of fibronectin-coated gelatin films by LOX cells.

Cells were seeded on chicken plasma fibronectin coupled to the surface of gelatin films. After cell culturing for the indicated times, cells were fixed, permeabilized, and labeled with fluorescein conjugates of goat anti-chicken fibronectin antibodies. Negative fluorescent spots under the cells at 6 hr indicate areas where fibronectin substrata have been removed, while darker spots seen at 1 day, 2 day, and 3 day represent areas where both fibronectin and the underlying crosslinked gelatin film have been removed. Note that the black spots increase in size as a function of time. (Bar=10 μm).

Figure 7:
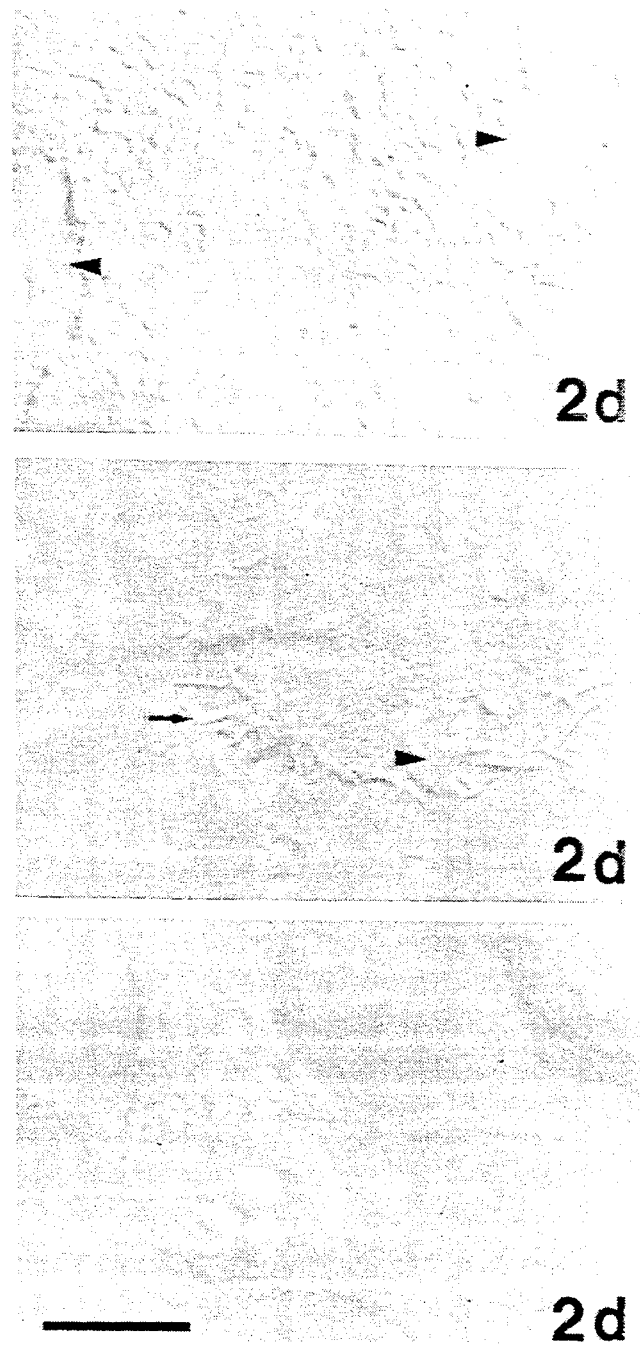
Figures 8D, 8E, 8F:
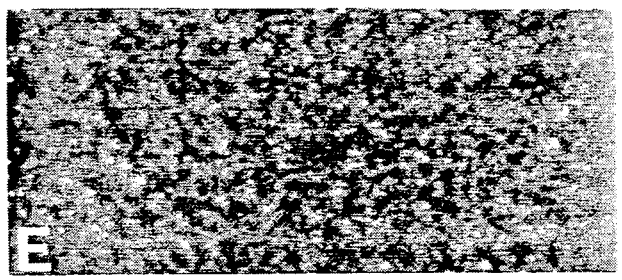
Figure 9A:
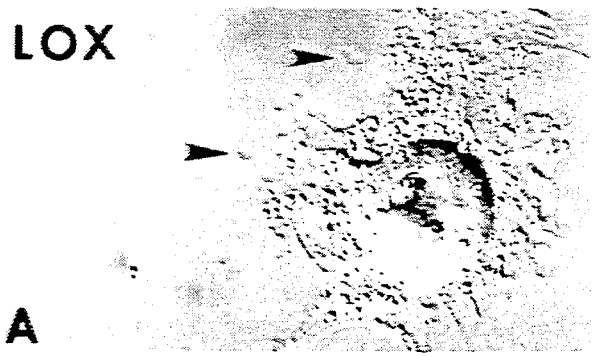
Figure 9B:
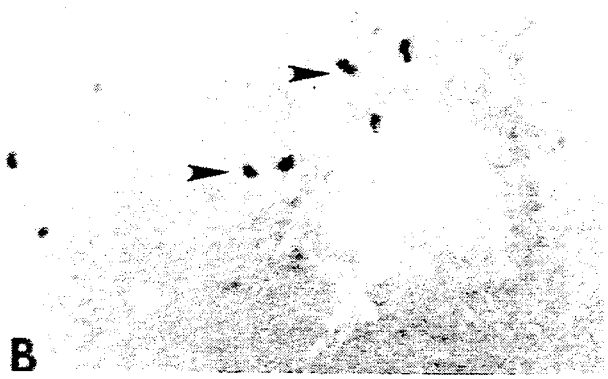
Figure 9C:
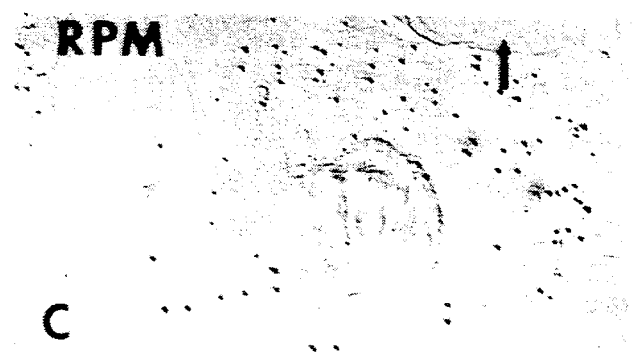
Figure 9D:
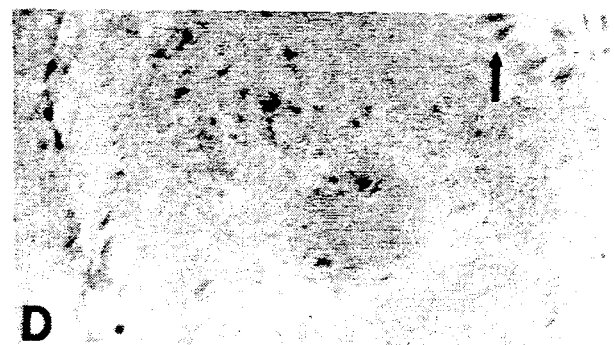
Figure 9E:
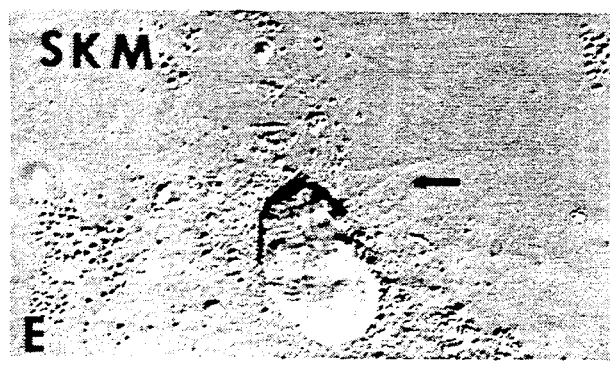
Figure 9F:

FIG. 7 shows a visualization of invasion sites of three human melanoma cell lines, LOX, RPMI7951, SK-MEL-28, into glutaraldehyde-crosslinked gelatin films.

DIC images of cell cultures show surface indentations on the film formed under both LOX and RPMI7951 cells but not SK-MEL-28 cells at 1 day and 2 days. (Bar=50 μm.)

FIGS. 8A, 8B, 8C, 8D, 8E and 8F show direct fluorescent visualizations of invasion sites of three human melanoma cell lines LOX, RPMI7951, and SK-MEL-28, into rhodamine-fibronectin coated gelatin films.

The cells were grown for 24 hrs on rhodamine-fibronectin conjugates which were previously coupled to fixed gelatin films. Black spots in fluorescent images (A, C, and E) indicate areas under both LOX and RPMI7951 cells but not SK-MEL-28 cells, where rhodamine-fibronectin substrate have been digested and removed. The corresponding DIC images of cell cultures (B, D, and F) show surface indentations on the film formed under both LOX and RPMI7951 cells but not SK-MEL-28 cells. (Bar=50 μm.)

FIGS. 9A, 9B, 9C, 9D, 9E and 9F show visualization of invasion sites of three human melanoma cells lines LOX, RPMI7951 and SK-MEL-28 into fibronectin-coated gelatin films.

Cells were grown for 6 hrs on chicken plasma fibronectin coupled to the surface of gelatin films. DIC images of cell cultures (A, C, and E) and the corresponding immunofluorescent images (B, D, and F) using indirect labeling with fluorescein conjugates of goat anti-chicken fibronectin antibodies, show black spots (arrowheads) on the film formed under both LOX and RPMI7951 cells but not SK-MEL-28 cells. Immunofluorescent images of all three cells also show black streaks (arrows) that represent areas of contacts between the cells and the substratum and are not accessible to antibody labeling. (Bar=50 μm.)

Figures 10A, 10B:
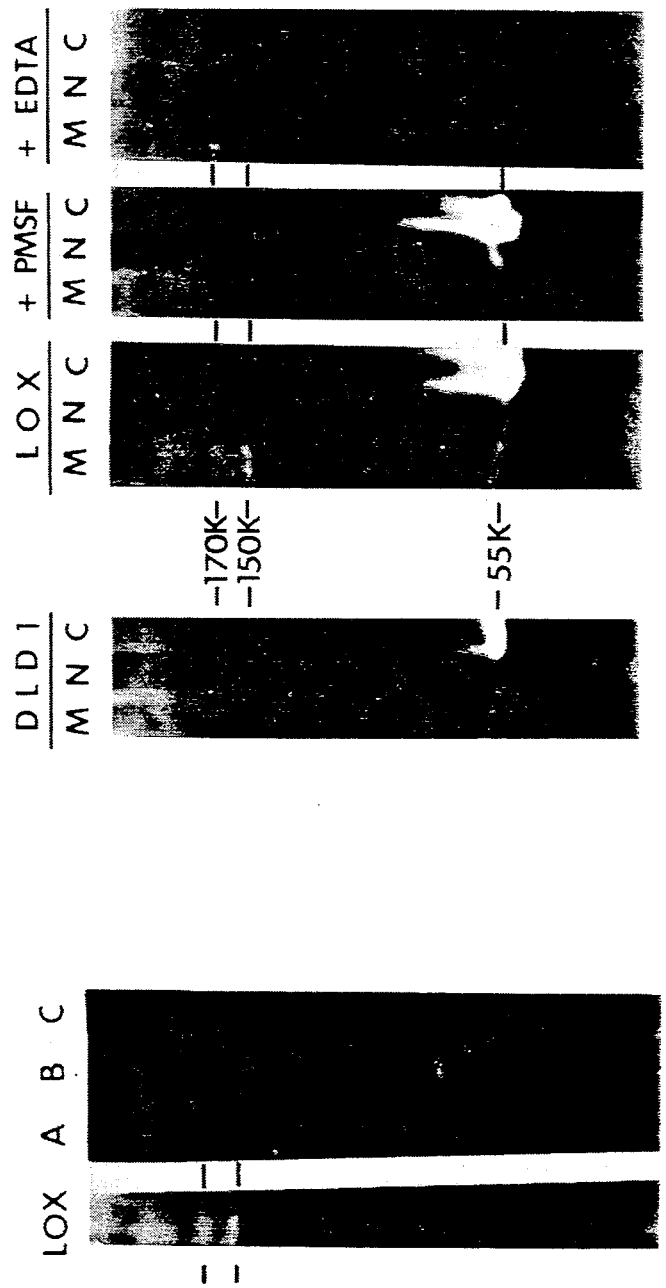

FIGS. 10A and 10B show the activation of 170 kD, 150 kD, and 55 kD gelatinases in the LOX membrane.

FIG. 10A shows gelatin-degrading activities of the membranes from LOX cells (LOX), SW620 (A), HT1080 (B), and EJ (C).

The detergent-soluble membrane fraction of these cells after storage at 4° C. for 3 d was analyzed on gelatin zymograms as described in FIG. 2. Doublet gelatinases with apparent molecular mass of 170 kD and 150 kD, and a low molecular mass 55 kD gelatinase are evidenced primarily in the membrane fraction of LOX cells but not in other tumor cells.

FIG. 10B shows gelatinase activities of subcellular fractions from LOX cells (LOX) and DLD1 cells (DLD1), and their inhibitor sensitivity.

The detergent-soluble membrane fraction (M), detergent-soluble nuclear fraction (N), and cytosol fraction (C) were prepared and subjected to gelatin zymography. Both 170 kD and 150 kD gelatinases are associated with LOX membranes, sensitive to the cysteine protease inhibitor PMSF and NEM, but insensitive to the metalloprotease inhibitor EDTA, while 55 kD gelatinases appeared in membrane and cytosol fractions of both LOX and DLD1 cells, were sensitive to the metalloprotease inhibitor EDTA, and were insensitive to PMSF and NEM.

FIGS. 11A and 11B show the identification of a 170 kD protease in subcellular fractions of LOX (L), RPMI7951 (R), and SK-MEL-28 (S) cells.

Gelatin zymogram of various subcellular fractions from LOX (L), RPMI7951 (R), and SK-MEL-28 (S) cells is shown. These fractions include detergent-soluble membrane fraction (M), detergent-soluble nuclear fraction (N), cytosol fraction (C), concentrated serum-free conditioned medium (MD), and octyl glucoside detergent extract of the 100,000× g pellet from conditioned medium (P). Approximately 30 μg of total protein was applied to each lane and subjected to gelatin zymography. Only membrane fraction (M) and the membrane derived from conditioned medium (P) of LOX and RPMI7951 cells show major negatively stained doublets with apparent molecular mass of 170 kD and 150 kD that represent complete digestion of immobilized gelatin by the proteases. The 55 kD gelatinase is present in the membrane derived from conditioned medium (P) of all three cells but not in other fractions of the cells. MW indicates the lane containing molecular mass standards.

Figure 12:
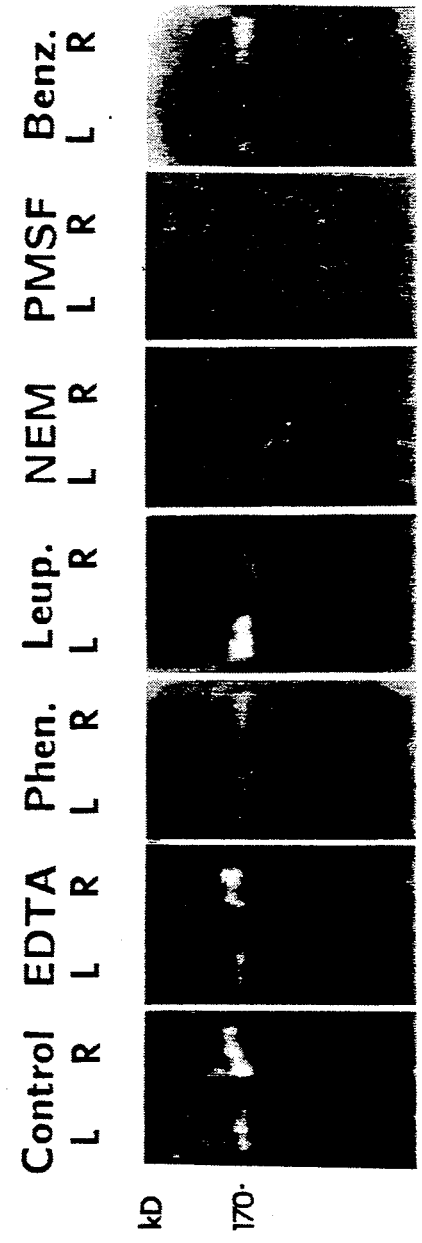

FIG. 12 shows the inhibitor specificity of the 170 kD protease in the membrane of LOX (L) and RPMI7951 (R) cells.

Prior to electrophoresis, the detergent soluble membrane fractions from both LOX and RPMI7951 cells were treated with various protease inhibitors. Slices of gelatin gels containing the 170 kD protease were prepared and incubated in HBSS containing various protease inhibitors. Concentrations of inhibitors were as follows: EDTA, 2 mM, 1,10-phenanthroline (Phen.), 2 mM, leupeptin (Leup.), 0.1 mM, NEM, 1 mM, PMSF, 1 mM, benzamidine (Benz.), 10 mM; and pepstatin (Pep.), 0.03 mM. The activity of the 170 kD protease was inhibited by NEM or PMSF, but not inhibited by 2 mM EDTA, 2 mM 1,10 phenanthroline, 0.1 mM leupeptin, 10 mM benzamidine, or 0.03 mM pepstatin.

Figure 13B:
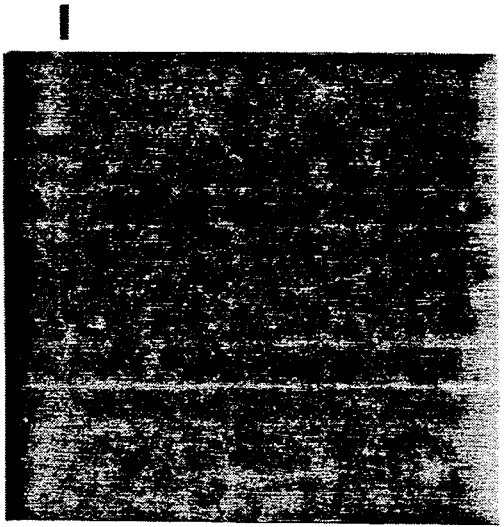
Figure 13A:
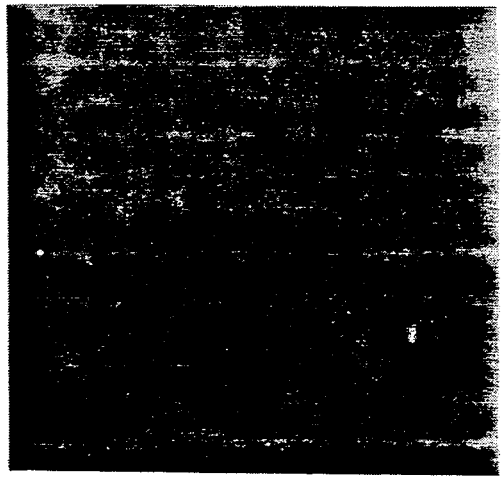

FIGS. 13A and 13B show the identification of the 170 kD protease in membrane fractions of the LOX tumor tissue derived from athymic nude mice as assayed on gelatin zymograms.

The 170 kD protease in different fractions of the Triton X-114-soluble material recovered from LOX tumor tissues, which were prepared in solutions lacking cations (Panel A) or containing 5 mM EDTA (Panel B). Approximately 10 μl of plasma of a tumor-bearing nude mouse was loaded in the first lane (PM). Subsequent lanes contained Triton X-114 detergent extract of the LOX tumor (TX), the aqueous phase (AQ) and detergent phase (DT) of the Triton X-114 detergent extract of the LOX tumor, and the WGA-binding material from the Triton X-114 detergent phase of the LOX tumor extract (WGA). Approximately 30 μg of total protein was applied to lanes TX, AQ, and DT, while only 2 μg of total protein was applied to lane WGA. They were analyzed by gelatin zymography. The 170 kD protease was partitioned into the detergent phase of the Triton X-114 extracts (DT), concentrating the 170 kD activity 12-fold over that of the total Triton X-114 detergent extract of the LOX tumor (TX). The 170 kD enzyme was enriched by WGA-beads a further 10-fold in specific activity (WGA) over that of the detergent phase of the Triton X-114 extracts (DT). The 55 kD metallo-gelatinase and other gelatinases lose their activity in the procedure ultilizing buffers lacking cations (Panel A) or containing EDTA (Panel B).

DETAILED DESCRIPTION OF THE PREFERRED EMBODIMENTS

It has been discovered that the morphologically defined invasiveness of tumor cells correlates with the presence of a specific membrane-associated protease. The invasiveness of human tumor cells has been assessed using crosslinked gelatin film culture (Chen, W.-T., Olden, K., Bernard, B. A. and Chu, F.-F. (1984), J. Cell Biol. 98, 1546-1555) and an invasive human melanoma cell line LOX (Fodstad, O., Aamdal, S., Mcmenamin, M., Nesland, J. M., and Pihl, A. (1988), Int. J. Cancer 41, 442-449) has been identified which shows a stable invasive phenotype in degrading crosslinked gelatin films in vitro. An additional invasive human malignant melanoma cell line RPMI7951 (Moore, G. (1977), J Nat. Cancer Inst. 59, 301-307) has also been identified which shows less degradation than LOX cells. The melanoma line SK-MEL28 (Carey, T. E., Takahashi, T., Resnick, L. A., Oettgen, H. F. and Old, L. J. (1976), Proc. Natl. Acad. Sci. U.S.A., 73, 3278-3282) and 32 other human tumor cell lines were negative in this in vitro invasion assay. Cell fractionation resolved three neutral proteases, a sulfhydryl-sensitive 170 kD gelatinase which can be cleaved to 170 kD and 150 kD forms, a 55 kD metallogelatinase and a plasminogen activator in association with the membrane of both LOX and RPMI7951 cells. The metallogelatinase and plasminogen activator were also found in other tumor cells which were non-invasive in vitro. The activity of the 170 kD membrane-associated protease is specific for the LOX and RPMI7951 cells. Although the precise role of the 170 kD protease in the activation of ECM degradation is unknown, it is postulated that its unique presence on the LOX membrane allows direct degradation of the ECM and may also initiate a cascade of proteolysis at the critical sites of contact between cells and the substratum (Chen, W.-T., Olden, K., Bernard, B. A. and Chu, F.-F. (1984), J. Cell Biol. 98, 1546-1555; Chen, W.-T. (1989), J. Exptl. Zool. 251, 167-185; Hebert, C. A., and Baker, J. B. (1988), J. Cell Biol. 106, 1241-1247; Pollanen, J., Hedman, K., Nielsen, L. S., Dano, K., and Vaheri, A. (1988), J. Cell Biol. 106, 87-95; Plow, E. F., Freany, D. E., Plescia, J., and Miles, L. A. (1986), J. Cell Biol. 103, 2411-2420; Stoppelli, M. P., Tacchetti, C., Cubellis, M. V., Hearing, V. J., Cassani, G., Appella, E., and Blasi, F. (1986), Cell 45, 675-684; Stephens, R. W., Pollanen, J., Tapiovaara, H. Leung, K. C., Sim, P. S., Salonen, E. M., Ronne, E., Behrendt, N., Dano, K., and Vaheri, A. (1989), J. Cell Biol. 108, 1987-1995). Using a combination of the in vitro invasion assay and cell fractionation, it has also been found that another human melanoma cell line RPMI7951 was invasive, but less invasive and expressed correspondingly less of the 170 kD membrane gelatinase than the LOX cells. In addition, the 170 kD protease was co-isolated with the ECM contact-enriched membrane of LOX. Thus the 170 kD protease correlates with cell invasiveness in the in vitro invasion assay. Other types of tumor cells which were tested and found negative in both the in vitro invasion assay and gelatinase activity measurement of the membrane fraction include esophageal squamous carcinoma TE2, colon adenocarcinoma cells such as DLD1 and SW620, bladder carcinoma EJ cells, pancreatic adenocarcinoma Capan-1 and Capan-2, fibrosarcoma cells HT1080, and lung fibroblasts transformed by SV40 virus WI-38 VA13.

It is thought that the 170 kD protease is an integral membrane protease since it is found in the detergent phase, but not in the aqueous phase of the Triton X-114-solubilized membrane fraction of LOX cells. The 170 kD protease is also present in the octylglucoside-solubilized membrane fraction of LOX cells, but not in the cytosol fraction or in supernatant from conditioned media. The activity of the 170 kD protease was also retained in membrane fractions following freezing and thawing and extraction with high-salt buffers. Additionally, the 170 kD protease was found in the detergent extracts of 100,000 xg pellets derived from conditioned media suggesting that the 170 kD protease is released into the medium in membrane vesicles (Zucker, S., Wieman, J. M., Lysik, R. M., Wilkie, D. P., Ramamurthy, N., and Lane, B. (1987), Biochim. Biophys. Acta., 924, 225-237).

Studies with inhibitors suggest that the 170 kD protease is a distinct enzyme from another membrane-associated protease, a cathepsin B-like activity previously identified in tumor cells (Poole, A. R., Tiltman, K. J., Recklies, A. D., and Stoker, T. A. (1980), Nature 273, 545-547; Sloane, B. F., Rozhin, J., Johnson, K., Taylor, H., Crissman, J. D., and Honn, K. V. (1986), Proc. Natl. Acad. Sci. U.S.A., 83, 2483-2487). The 170 kD protease is a WGA-binding glycoprotein, characteristic of many integral membrane proteins, but cathepsin B is not (Barrett, A. J. (1973), Biochem. J. 131, 809-822; Barrett, A. J. (1977), Cathepsin B and other thiol proteinases. In Proteinases in mammalian cells and tissues, ed. Barrett, A. J. (Elsevier, Amsterdam), pp. 181-208). The 170 kD protease is also different from known cysteine proteases such as cathepsin B, L or H in terms of molecular weight, optimal pH and inhibitor specificity.

The 170 kD protease is a high molecular weight protease as determined by SDS-PAGE zymography and molecular sieve chromatography on Sephacryl S-200. The proteolytic activity is active at neutral pH and is enhanced by EDTA and DTT. In comparison with the prototype cysteine protease cathepsin B the 170kD gelatinase was insensitive to 0.1 mM leupeptin, 1 mM iodoacetic acid, 1 mM iodoacetamide, 0.02 mM E-64, 0.02 mM Z-Phe-Ala-CHN$_2$ or 0.02 mM Z-Phe-Phe-CHN$_2$. The 170 kD protease of the present invention was sensitive to other inhibitors, NEM, HgCl$_2$ and PMSF which bind the sulfhydryl group of amino acid residues. The inhibition by HgCl$_2$ and PMSF could be recovered by adding DTT and cysteine.

Figure 1:
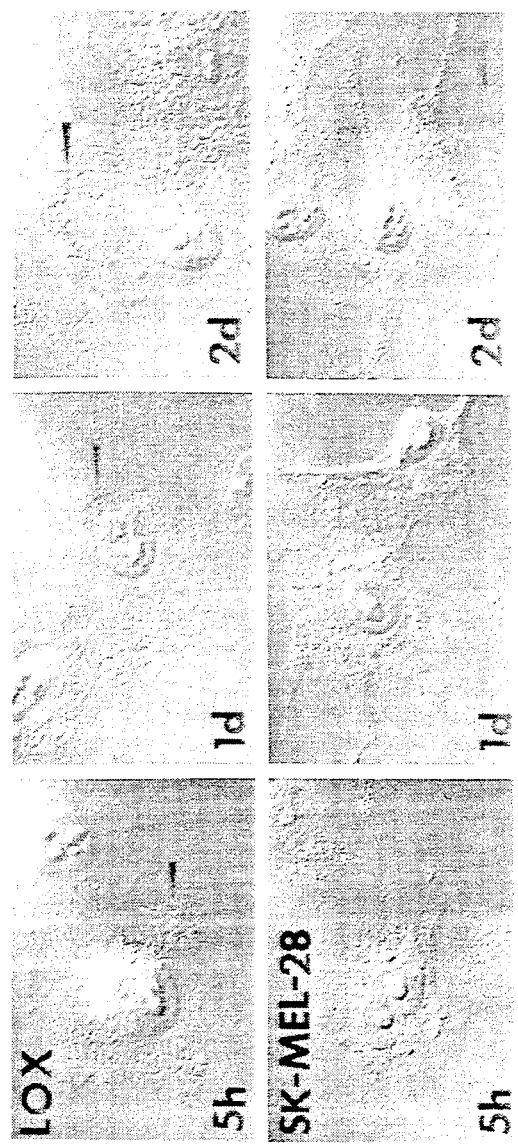
FIG. 1 shows a visualization of invasion sites of two human melanoma cell lines LOX and SK-MEL-28 into glutaraldehyde-crosslinked gelatin films.

In serum-containing medium, the crosslinked gelatin film remained unchanged when incubated without cells or with the control melanoma line SK-MEL28 (FIG. 1) and other human tumor cells. However, growth of LOX cells on the crosslinked gelatin film resulted in the appearance of surface indentations beneath the cells in a time-dependent manner (FIG. 1). More than 10% of LOX cells invaded the film at sites of cell contact 3 h after cell plating, and more than 30% at 5 h. The degraded spots increase in size as a function of time, such that large holes of more than 10 μm in diameter formed after 1 day (FIG. 1). When LOX cells were cultured on a fluorescently labeled fibronectin-coated substratum, the cells formed discrete spots lacking fluorescent fibronectin beneath the cells prior to the formation of morphological indentations in the gelatin film (FIG. 6). The appearance of these fibronectin-negative spots corresponds to an overall release of radio-labeled fibronectin into the medium as shown in chicken embryonic cells transformed by Rous sarcoma virus (Chen, W.-T., Olden, K., Bernard, B. A. and Chu, F.-F. (1984), J. Cell Biol. 98, 1546-1555). The observed ECM-degrading activity of LOX cells, however, is lacking when the cells were cultured in serum-free media. The possibility that activation of cell surface plasminogen activator is directly involved in the localized degradation of the ECM by LOX cells was tested. LOX cells degraded the fibronectin-gelatin film when the cells were cultured in media containing 5% plasminogen-depleted serum prepared as described (Deutsch, D. G., and Mertz, E. T. (1970), Science 170, 1095-1096) and 20 mM ε-aminocaproic acid. Thus, the plasmin-dependent protease cascade is not essential for the capacity of LOX cells to degrade the ECM and invade the glutaraldehyde-fixed gelatin film. The LOX invasive phenotype appears to be stable as no change in this cell surface proteolytic activity during a period of two years has been detected.

To determine whether the observed ECM degradation by LOX cells is due to proteases associated with the plasma membrane, subcellular fractions from LOX cells, RPMI7951, and the control melanoma line SK-MEL28 were prepared, and assayed for proteolytic activities by ECM substrate zymography. FIG. 2 shows that, on gelatin zymograms, a prominent negative staining band with apparent Mr of 170,000 was present in the detergent-soluble membrane fraction of LOX cells but not of SK-MEL28 cells. The membranes recovered from culture media conditioned with LOX also had the 170kD gelatinase but it was not found with SK-MEL28 (FIG. 2A) and other tumor cells. The 170 kD protease was also found in the membranes from nuclear fractions, but was found neither in cytosol and media fractions from LOX cells nor in any fraction from SK-MEL28 (FIG. 2A). To demonstrate the effectiveness of gelatin zymography in detecting proteases, decreasing amounts of total protein (60, 30, 15, 7.5, and 3.8 μg) from LOX membranes that had been solubilized in Laemmli SDS sample buffer without β-mercaptoethanol reduction by gelatin zymography (FIG. 2B) and conventional SDS-PAGE were tested.

The 170 kD gelatinase in LOX membranes cannot completely degrade fibronectin, fibrin or casein as shown by substrate zymography (FIG. 3). Using fibrin overlay gels in the presence and absence of plasminogen to determine the activity of plasminogen activator and fibrin-degrading enzymes, respectively, a 55 kD plasminogen activator in the membrane, and both the 55 kD plasminogen activator and a 110 kD fibrin-degrading protease in the cytosol of LOX cells was found (FIG. 3). In addition, a low molecular weight 55 kD gelatinase, that was sensitive to the metalloprotease inhibitor EDTA, was found in various amounts from different preparations, most abundantly in the cytosol fraction of tumor cells (FIG. 3). These proteases including the 55 kD metallo-gelatinase and 55 kD plasminogen activator were also found in the membranes of some tumor cells such as DLD1 that are negative in the in vitro invasion assay (FIG. 7B).

The 170 kD gelatinase represents the major protease in the membrane of LOX cells and can be partially purified by Sephacryl S-200 gel filtration and WGA-agarose affinity chromatography (FIGS. 4A, 4B). Approximately 3 units of activity of the 170 kD protease was obtained with S-200 gel filtration (FIG. 4A), contained in 10 μg of protein. One unit of activity is defined as the amount of activity giving the same density on a zymogram as the band shown in the 30 μg lane of FIG. 2B which was derived from 30 μg of protein from the total membrane extract. Thus, an approximate threefold increase in specific activity was achieved. The material recovered from the WGA-column was enriched in 170 kD activity an additional 10-fold (FIG. 4B). These combined procedures produced an overall 30-fold enrichment of the 170 kD protease compared to the octylglucoside-soluble membrane extract as determined by measurements of total protein and enzymatic activity on gelatin zymograms. A low molecular weight, 55 kD metalloprotease was removed by passing the LOX membrane extracts over S-200 gel filtration and WGA columns (FIGS. 4A, 4B).

The 170 kD gelatinase was also found in a Triton X-114 extract of the LOX cell layer (FIG. 4C). The 170 kD gelatinase was partitioned into the detergent phase of the Triton X-114 extracts (FIG. 4C), producing a 10-fold enrichment of the 170 kD protease compared to the total Triton X-114 detergent extract of the LOX cell layer. The 170 kD protease obtained by binding to WGA could also be partitioned into the detergent phase of the Triton X-114 extracts. These data suggest that the protease is an integral membrane protein. The 170 kD gelatinase from WGA binding proteins of LOX cell membranes bound to an organomercurial adsorbent, suggesting its role as a possible cysteine protease (Barrett, A. J. (1973), Biochem. J. 131, 809–822).

The 170 kD protein was active when the samples were incubated at room temperature and at 37° C., whereas it was inactivated after incubation at 55° C. for 10 min or boiling for 2 min (FIG. 5A). The gelatinase activity of 170 kD protein was enhanced slightly by pre-incubation with β-mercaptoethanol and its apparent molecular weight remained at 170 kD under the reducing condition (FIG. 5A). To determine the pH optima of the 170 kD proteases, strips of gelatin zymograms containing the 170 kD gelatinase were incubated in Hank's balanced salt solution (HBSS) adjusted to various pH values and gelatinase activity of the 170 kD protein was examined.

As shown in FIG. 5B, the 170 kD gelatinase from LOX cells was active in the range from pH 6 to pH 8.4, with its optimal pH at pH 7. To classify the 170 kD protease, the effects of various protease inhibitors specific for serine-, aspartate-, cysteine-, or metalloproteases on the gelatin-degrading activity of the 170 kD protein were examined. FIG. 5C show the sensitivity of the 170 kD gelatinase to various protease inhibitors. Inhibitors of the aspartate-, serine-, or metalloproteases including pepstatin (0.03 mM), benzamidine (10 mM), EDTA (5 mM) and 1,10 phenanthroline (2 mM), had no discernible effect on the activity of the 170 kD protein. However, treatment of the sample with a mixture of EDTA (2 mM) and DTT (2 mM) which inhibits metal-dependent proteases and activates cysteine proteases, significantly enhance the activity of the 170 kD protein. The 170kD gelatinase was inhibited by 1 mM N-ethylmaleimide (NEM) or 1 mM phenylmethanesulfonyl fluoride (PMSF), but PMSF-inhibitable activity could be recovered by 10 mM DTT (FIG. 5C, lane PMSF+DTT).

Table I summarizes results of inhibition of the 170 kD gelatinase. The 170 kD protease could also be inhibited by 0.2 mM HgCl2, and the HgCl2-inhibitable activity could be recovered by 5 mM cysteine (Table I). This inhibition data is consistent with the binding of the 170 kD to the organomercurial absorbent. In comparison with the prototype cysteine protease cathepsin B, however, the 170 kD gelatinase was insensitive to 0.1 mM leupeptin, 1 mM iodoacetic acid, 1 mM iodoacetamide, 0.02 mM trans-epoxysuccinyl-L-leucylamido- (4-guanidino)-butane (E-64), 0.02 mM benzyloxycarbonyl-L- phenylalanyl-L-alanine-diazomethane (Z-Phe-Ala-CHN2), or 0.02 mM benzyloxycarbonyl-L-phenylalanyl-L-phenylalanine-diazomethane (Z-Phe-Phe-CHN2).

This inhibition data together with the data on binding of the 170 kD to the organomercurial absorbent show that the active site of the 170 kD protease involves a sulfhydryl group.

TABLE I

Characterization of the Activity of 170kD Protease from LOX Cells by Gelatin Zymography

| Treatment | Relative Activity[2] |
|---|---|
| Temperature | |
| 22–37° C. 30–60 min | +++ |
| 55° C. 10 min | − |
| 100° C. 2 min | − |
| Reduction at 37° C. | +++ |
| Beta-mercaptoethanol, 2.5% | |
| PH range | |
| 3.0–5.5 | − |
| 6.0 | + |
| 6.5 | ++ |
| 6.8–7.2 | +++ |
| 7.5–8.4 | ++ |
| 8.7–10.0 | − |
| Inhibitors[1] | |
| Pepstatin (0.03 mM) | +++ |
| EDTA (5 mM) | +++ |
| EDTA (2 mM) + DTT (2 mM)[3] | ++++ |
| 1,10 phenanthroline (2 mM) | +++ |
| Benzamidine (10 mM) | +++ |
| PMSF (1 mM) | − |
| PMSF (1 mM) + DTT (10 mM) | ++ |
| Leupeptin (0.1 mM) | +++ |
| HgCl2 (0.2 mM) | − |
| HgCl2 (0.2 mM) + cysteine (5 mM) | ++ |
| N-ethylmaleimide (1 mM) | − |
| Iodoacetic acid (1 mM) | +++ |
| Iodoacetamide (1 mM) | +++ |
| E-64 (0.02 mM) | +++ |
| CBZ-Phe—Ala—CHN2 (0.02 mM)[4] | +++ |
| CBZ-Phe—Phe—CHN2 (0.02 mM)[5] | +++ |

[1]In all cases when only individual inhibitors were applied, detergent-soluble membrane fractions from LOX cells were first treated with protease inhibitors at 37° C. for 30 min prior to electrophoresis, and individual lanes were cut out and incubated in HBSS containing the protease inhibitor at the same concentration as in the pre-treated sample. In cases of two inhibitors indicated in the Table, the first inhibitor was used prior to electrophoresis and the second inhibitor was applied during the incubation of the sample in gelatin zymogram. Inhibition of protease activity was evaluated by the appearance of negative-staining bands in gelatin zymograms.
[2]Relative Activity shown was results of three independent experiments.
[3]A mixture of EDTA (2 mM) and DTT (2 mM) was used.
[4]CBZ-Phe—Ala—CHN2 is a specific inhibitor for cathepsin B.
[5]CBZ-Phe—Phe—CHN2 is a specific inhibitor for cathepsin L.

The 170 kD protease of LOX cells appears to have two active forms. After the detergent-soluble membrane fraction of LOX cells were stored at 4° C. for more than 2 days a doublet of gelatinases with apparent molecular mass of 170 kD and 150 kD, and a low molecular weight 55 kD gelatinase appeared in the membrane (FIG. 10A). The 170 kD and 150 kD gelatinases were sensitive to the cysteine protease inhibitors PMSF and NEM (FIG. 10B), but they appeared to be active in the presence of EDTA and DTT (FIG. 10B). The 55 kD protease is a metallo-gelatinase as its activity was blocked by EDTA (FIG. 10B). The 170 kD and 150 kD proteases were found in the membranes of LOX (FIG. 10) and RPMI7951 cells (FIG. 11), while the 55 kD protease was found in various amount from the membranes and cytosol of many tumor cells (FIG. 10B). These proteases were not found in the membranes of SK-MEL-28 and other tumor cells SW620, HT1080, and EJ (FIG. 10A). The combined association of the 170 kD and 150 kD gelatinases, the 55 kD metallogelatinase, and the 55 kD plasminogen activator with LOX membranes could account for activated ECM degradation by LOX cells that leads to the expression of cell invasiveness.

Figure 11:
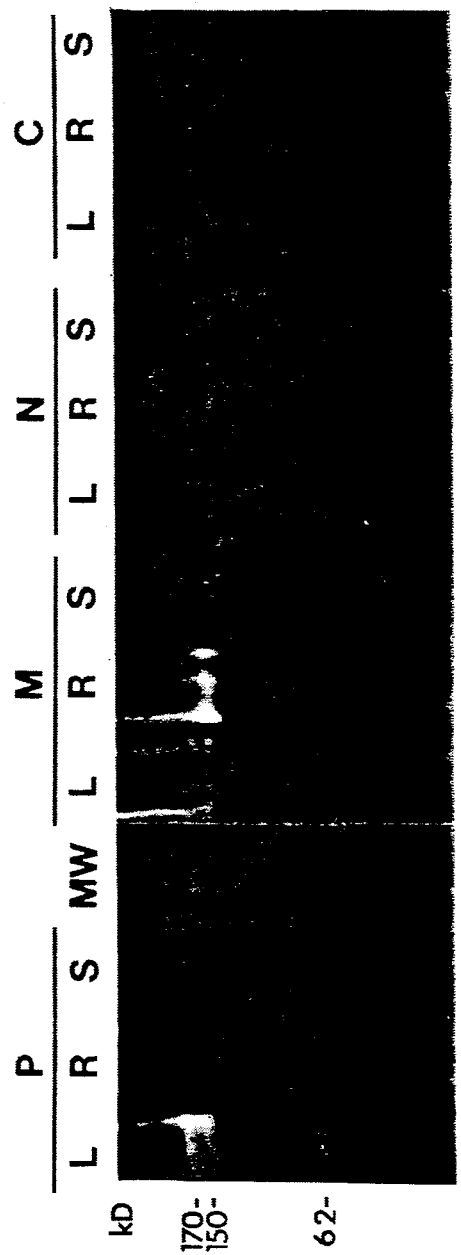

Further study has included a human melanoma cell line RPMI7951 (Moore, G. (1977), J Nat. Cancer Inst. 59, 301–307). Using the in vitro invasion assays by growing LOX, RPMI7951, and SK-MEL-28 cells on crosslinked gelatin films (FIG. 7), rhodamine-fibronectin coated gelatin films (FIG. 8), and fibronectin-coated gelatin films (FIG. 9), it has been found that both LOX and RPMI7951 cells were invasive, but RPMI7951 cells were less invasive than LOX cells. In relating cell invasiveness with the presence of specific ECM-degrading proteases, it has also been found that only membrane fraction and the membrane derived from conditioned medium of LOX and RPMI7951 cells show major negatively stained doublets with apparent molecular mass of 170 kD and 150 kD but SK-MEL-28 cells lack these proteases (FIG. 11). The 55 kD gelatinase is present in the membrane derived from conditioned medium of all three cells but not in other fractions of the cells (FIG. 11). The 170 kD and 150 kD proteases of LOX and RPMI7951 cells appear to have similar inhibitor specificity (FIG. 12), suggesting the identity of these proteases.

The procedure for measuring the 170 kD protease in isolated tumor cells has been found to be useful in the identification of the 170 kD protease of LOX tumor growing in athymic nude mice using gelatin zymography (FIG. 13). It has been found that the 170 kD protease was partitioned into the detergent phase of the Triton X-114 tumor extracts, concentrating the 170kD activity 12-fold over that of the total Triton X-114 detergent extract of the LOX tumor (FIG. 13). The 170 kD enzyme was enriched by WGA-beads a further 10-fold in specific activity over that of the detergent phase of the Triton X-114 tumor extracts (FIG. 13). The 55 kD metallo-gelatinase and other gelatinases lose their activity in this procedure since all solutions contain EDTA or lack cations (FIG. 13). These combined procedures produced an overall 120-fold enrichment of the 170 kD protease compared with the Triton X-114-soluble tumor extract as determined by measurements of total protein and enzymatic activity on gelatin zymograms. Each assay requires a minimal of 1 mg of tumor mass or 100 µl of the plasma.

Utility of Obtained Membrane Proteases

Although many enzymes, including collagenases, stromelysin, plasminogen activator, glycosidases and heparinases, have been shown to be secreted in an elevated level in malignantly transformed cells as compared with their normal counterparts, the membrane protease of the present invention appears to be closely associated with malignant transformation of cells. Since the presence of the membrane protease antigens is useful for demonstrating malignant cells with invasive capacity through the extracellular matrix, the enzyme or enzyme complex can be of great diagnostic value in detecting the presence of cancer or tumors in mammals. As used herein, mammals include animals, such as domestic, laboratory, livestock animals, etc. as well as humans. The measurement of the membrane protease activity can be accomplished in isolated tumor cells and biological fluids, such as plasma or tumor tissue extracts. The membrane protease complex also shows promise in industrial applications, for example, for the identification and purification of commercially valuable materials found in tumor membrane mixtures difficult to resolve by other than proteolytic assays in the present application.

In certain applications the membrane protease may be used for identification and production of functional inhibitors. For example, certain chemicals and synthetic peptides block the activity of metalloendoproteases and serine-proteases and inhibit the invasion of tumor cells through the extracellular matrix. Thus, the membrane protease may be separated in substrate SDS gels or bound to a solid phase, and used in identification of specific inhibitors.

In other applications the membrane protease may be isolated in enriched forms, such as in a particular membrane fraction or a band in SDS gels, and used as an immunogen for production of specific monoclonal antibodies directed against these proteases. The use of purified forms of protease undoubtedly increases the chance of successful production of monoclonal antibodies.

EXAMPLES

Cell Culture. The human amelanotic melanoma cell line LOX (was maintained with 1:1 mixture of Dulbecco's modified Eagle media and RPMI 1640 media supplemented with 10% calf serum, 5% Nu-serum (Collaborative Research Inc. Mass.), 2 mM L-glutamine, 1 unit/ml penicillin, 10 µg/ml streptomycin. The human melanotic melanoma cell line SK-MEL28 was maintained in Eagle's minimum essential medium supplemented with 10% fetal calf serum, 1 mM sodium pyruvate and 0.1 mM non-essential amino acids, 2 mM L-glutamine, 1 unit/ml penicillin, 10 µg/ml streptomycin. LOX and EJ cells were obtained from Dr. L. B. Chen, Dana-Farber Cancer Institute, Harvard Medical School. Other human tumor cell lines including RPMI DLD1, SW620, SK-MEL28, and HT1080 cells were purchased from the American Type Culture Collection (Rockville, Md.).

Cell Assays for Localized Degradation of the Glutaraldehyde-Crosslinked Gelatin Film by Tumor Cells. Glutaraldehyde-crosslinked gelatin films coated on glass coverslips that were surface-coupled with fibronectin were prepared (Chen, W.-T., Olden, K., Bernard, B. A. and Chu, F.-F. (1984), J. Cell Biol. 98, 1546-1555). Morphological identification of localized degradation of crosslinked gelatin films by tumor cells was done by differential interference contrast (DIC) microscopy using a Zeiss Photomicroscope III (Carl Zeiss, Inc., New York).

Protease Assays and Gelatin Zymography. A detergent-soluble membrane fraction, a detergent-soluble nuclear fraction, and a water-soluble cytosol fraction were prepared (Quigley, J. P. (1976), J. Cell Biol. 71, 472-486; Chen, J.-M. and Chen, W.-T. (1987), Cell 48, 193-203). Serum-free conditioned media derived from cell culture were spun at low speed to remove floating cells and cell debris. Membranes from conditioned media were collected by centrifugation at 100,000 xg for 1 hr at 4° C., and then extracted in 2% octylglucoside in Tris-buffered saline (TBS; 50 mM Tris-HCl, pH 7.4/150 mM NaCl) (Zucker, S., Wieman, J. M., Lysik, R. M., Wilkie, D. P. Ramamurthy, N., and Lane, B. (1987), Biochim. Biophys. Acta. 924, 225-237), or extracted in 1% Triton X-114 in TBS then partitioned into detergent and aqueous phases (Bordier, C. (1981), J. Biol. Chem. 256, 1604-1607). Total protein concentrations of various fractions were determined by BCA assay (PIERCE Chemical Co., Ill.), using bovine serum albumin solutions as standards.

To analyze degradation of immobilized ECM proteins after SDS-PAGE, substrate zymography (Chen, J.-M. and Chen, W.-T. (1987), Cell 48, 193-203; Heussen, C., and Dowdle, E. B. (1980), Anal. Biochem. 102, 196-202) and fibrin overlay zymography (Granelli-Piperno, A., and Reich, E. (1978), J. Exp. Med. 148, 223–234) were used. For substrate zymograms, protease substrates were gelatin (3 mg/ml, denatured type I collagen, SIGMA), casein (2 mg/ml, SIGMA), or human plasma fibronectin (0.5 mg/ml, New York Blood Center Inc., N.Y.). Fibrin overlay zymography was used to detect plasminogen activators and fibrinolytic proteases in the cellular fractions. Cellular proteins were first separated by electrophoresis on a 6% SDS-polyacrylamide gel without reduction. The gel was washed with 2.5% Triton X-100, and then overlaid an additional 1.25% agarose gel which contained 2.5 mg/ml fibrinogen (essentially plasmin free, SIGMA), 0.4 U/ml human thrombin (SIGMA), and 27 µg/ml plasminogen (SIGMA). After incubating at 37° C. overnight, the fibrin-agarose gel was fixed and stained with 0.1% amido black in 70% methanol and 10% acetic acid. Plasminogen activators and fibrinolytic proteases were demonstrated as negative bands in the fibrin gel.

Column Chromatography. The 170 kD gelatinase was partially purified by molecular sieve chromatography on a Sephacryl S-200 column (Pharmacia LKB Biotechnology Inc., N.J.). The LOX membrane fraction (2.5 ml sample volume) which had been prepared in the absence of EDTA was loaded onto an Sephacryl S-200 column (1.5×70 cm) equilibrated in 1% octylglucoside in TBS at 4° C. The column was eluted with the same octylglucoside buffer at a flow rate of 8 ml/h and 2.4-ml fractions collected. Fractions showing absorbence at 280 nm were analyzed by gelatin zymography and those containing the 170 kD protease were pooled for further purification.

The above fractions containing the 170 kD protease were mixed with WGA-Agarose (VECTOR Laboratories Inc., Calif.) by rotating overnight at 4° C. The WGA-Agarose mixture was packed in a column, and the column was washed with 3 column volumes of 1% octylglucoside, 200 mM NaCl, and 5 mM EDTA in 10 mM Tris-HCl pH 7.5. Adsorbed WGA-binding proteins were then eluted with 2 column volumes of 0.5 M N-acetyl-D-glucosamine (SIGMA), 1% octylglucoside, 200 mM NaCl, and 5 mM EDTA in 10 mM Tris-HCl pH 7.5 (Kelly, T., Molony, L., and Burridge, K. (1987), J. Biol. Chem. 262, 17189–17199). Fractions containing proteins were combined, and subjected to gelatin zymography.

Protease Inhibitors. Specific inhibitors for various proteases were included in gelatin zymography for the inhibition of the 170 kD protease. The samples were preincubated with various inhibitors at 37° C. for 30 min before applying to the gelatin gel for electrophoresis. Following electrophoresis and washing, the gel slices were incubated in HBSS containing the same protease inhibitors as those used for pretreatment at 37° C. overnight. These inhibitors are: PMSF, benzamidine, 1,10 phenanthroline, EDTA, N-ethylmaleimide (NEM), HgCl$_2$, cysteine, iodoacetic acid, iodoacetamide, trans-epoxysuccinyl-L-leucylamido-(4-guanidino)-butane (E-64) (SIGMA Chemical Co. Mo.), dithiothreitol (DTT) (SERVA Feinbiochemica, N.Y.), leupeptin, pepstatin (Peninsula Laboratories, INC. Calif.), benzyloxycarbonyl-L-phenylalanyl-L-alanine-diazomethane (Z-Phe-Ala-CHN$_2$), and benzyloxycarbonyl-L-phenylalanyl-L-phenylalanine-diazomethane (Z-Phe-Phe-CHN$_2$) (Enzyme System Products, Calif.).

Animals and LOX Tumors. Female specific-pathogen-free Balb/c athymic nude mice (NU/NU homozygous) were obtained from Taconic Farms, Inc. (Germantown, N.Y.) and were first used at 6 to 9 weeks of age. The mice were housed in a contained facility within laminar flow filtered air containment cabinets and fed sterilized water and mouse chow. LOX tumor growth was performed by the subcutaneous injection of $1 \times 10^6$ tumor cells in 0.2 ml of warm, serum-free RPMI 1640 into the flank of the animal (Fodstad et al., (1988). Int. J. Cancer, 41, 442–449). The mice grew tumors of 18 mm in diameter approximately 12 days after the injection. The mice were sacrificed and their tumors and plasma were collected for both microscopical and biochemical analysis.

Summary of the Identification and Isolation of the 170 kD Protease from Isolated Tumor Cells, Plasma or Tumor Tissues Isolated tumor cells ($4 \times 10^7$ cells), plasma (0.1 ml) or tumor tissues (0.1 gm) were collected and then extracted in 1% Triton X-114 in Tris-buffered saline (TBS; 50 mM Tris-HCl, pH 7.4/150 mM NaCl) containing 5 mM EDTA. The total Triton X-114 detergent extracts of cells or tissues were partitioned into detergent and aqueous phases (Bordier, C. (1981) J. Biol. Chem. 256, 1604–1607).

The above detergent fraction containing the 170kD protease was mixed with 10 µl of wheat germ agglutinin (WGA)-agarose (Vector Laboratories) by rotating at 4° C. for 30 min. Adsorbed WGA binding proteins were then eluted with 100 µl of Laemmli sample buffer without reducing agent and incubated at 25° C. for 30 min. Fractions containing 10 µl of Laemmli sample buffer eluate were subjected to gelatin zymography. Each assay requires a minimal of 1 mg of tumor mass or 100 µl of the plasma.

In order to isolate the 170 kD protease for use as an immunogen and for the analysis of primary peptide sequence, adsorbed WGA binding proteins were eluted with 2 column volumes of 0.5 M N-acetyl-d-glucosamine (Sigma)/1% octyl glucoside/200 mM NaCl/5 mM EDTA in 10 mM Tris-HCl, pH 7.5 (Kelly, T., Molony, L. & Burridge, K. (1987) J. Biol. Chem. 262, 17189–17199). Fractions containing proteins were combined and the 170 kD gelatinase from WGA binding proteins of cell extracts bound to an organomercurial adsorbent (Barrett, A. J. (1973) Biochem. J. 131, 809–822). The 170 kD enzyme was enriched by organomercurial adsorbent a further 20-fold in specific activity over that of the WGA binding proteins. These combined procedures produced an overall 2,400-fold enrichment of the 170 kD protease compared with the Triton X-114-soluble tumor extracts as determined by measurements of total protein and enzymatic activity on gelatin zymograms.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A purified protease having a molecular weight as determined by SDS-PAGE of 170 kD, wherein said protease is
enzymatically active against gelatin, collagens, and fibronectin,
active in the pH range from 6 to 8.4 having an optimal pH at pH 7,
enhanced by EDTA and dithiothreitol, inhibited by the cysteine protease inhibitors, N-ethylmaleimide, HgCl$_2$, and phenylmethylsulfonyl fluoride, not inhibited by pepstatin, benzamidine, EDTA, 1,10-phenanthroline, leupeptin, iodoacetic acid, iodoacetamide, E-64, Z-Phe-Ala-CHN$_2$, or Z-Phe-Phe-CHN$_2$, and binds to an organomercurial adsorbent.

2. A purified protease having a molecular weight as determined by SDS-PAGE of 170 kD, wherein said protease is enzymatically active against gelatin, collagens, and fibronectin, active in the pH range from 6 to 8.4 having an optimal pH at pH 7, enhanced by EDTA and dithiothreitol, inhibited by the cysteine protease inhibitors, N-ethylmaleimide, HgCl$_2$, and phenylmethylsulfonyl fluoride, not inhibited by pepstatin, benzamidine, EDTA, 1,10-phenanthroline, leupeptin, iodoacetic acid, iodoacetamide, E-64, Z-Phe-Ala-CHN$_2$, or Z-Phe-Phe-CHN$_2$, and binds to an organomercurial adsorbent, said protease being obtainable by a process comprising:

culturing LOX or RPMI7951 cells, or collecting the plasma or tumor tissue from a LOX or RPMI7951 tumor-bearing mammal, contacting said cells, plasma or tissue with an aqueous detergent solution, partitioning the aqueous detergent solution into an aqueous phase and a detergent phase, contacting said detergent phase with wheat germ agglutinin-agarose to adsorb said protease onto said agglutinin, eluting said adsorbed protease from said wheat germ agglutinin, binding said eluted protease to an organomercurial adsorbent, and isolating said purified protease from said organomercurial.

3. The protease of claim 2, wherein said detergent is Triton X-114.

4. The protease of claim 2, wherein said adsorbed protease is eluted with N-acetyl-D-glucosamine.

* * * * *